United States Patent
Lepow et al.

(10) Patent No.: US 8,092,547 B2
(45) Date of Patent: Jan. 10, 2012

(54) SUBTALAR IMPLANT ASSEMBLY

(75) Inventors: Gary M. Lepow, Houston, TX (US);
Rebecca Wahl, Escondido, CA (US);
Louise M. Focht, Del Mar, CA (US)

(73) Assignee: Tornier, Inc., Edina, MN (US)

( * ) Notice: Subject to any disclaimer, the term of this patent is extended or adjusted under 35 U.S.C. 154(b) by 1178 days.

(21) Appl. No.: 11/049,413

(22) Filed: Feb. 1, 2005

(65) Prior Publication Data

US 2005/0177243 A1    Aug. 11, 2005

Related U.S. Application Data

(60) Provisional application No. 60/543,728, filed on Feb. 10, 2004.

(51) Int. Cl.
*A61F 2/42* (2006.01)
(52) U.S. Cl. ............. 623/21.18; 623/21.11; 623/53
(58) Field of Classification Search ........... 623/21.11, 623/53; 606/329
See application file for complete search history.

(56) References Cited

U.S. PATENT DOCUMENTS

| | | | | |
|---|---|---|---|---|
| 3,550,255 | A | * | 12/1970 | Skierski ............... 29/557 |
| 5,360,450 | A | | 11/1994 | Giannini |
| 5,741,253 | A | | 4/1998 | Michelson |
| 5,776,196 | A | | 7/1998 | Matsuzaki et al. |
| 5,824,106 | A | | 10/1998 | Fournol |
| 6,022,352 | A | * | 2/2000 | Vandewalle .......... 606/286 |
| 6,168,631 | B1 | | 1/2001 | Maxwell et al. |
| 6,183,519 | B1 | | 2/2001 | Bonnin et al. |
| 6,210,412 | B1 | * | 4/2001 | Michelson ............ 606/86 A |
| 6,488,712 | B1 | | 12/2002 | Tornier et al. |
| 6,824,567 | B2 | | 11/2004 | Tornier et al. |
| 2002/0072801 | A1 | * | 6/2002 | Michelson .......... 623/17.11 |
| 2003/0028198 | A1 | | 2/2003 | Tornier et al. |
| 2007/0162025 | A1 | | 7/2007 | Tornier et al. |
| 2007/0173947 | A1 | | 7/2007 | Ratron et al. |
| 2007/0270718 | A1 | | 11/2007 | Rochetin et al. |

OTHER PUBLICATIONS

U.S. Appl. No. 11/871,809, filed Oct. 12, 2007.
Dockery, Gary L. et al., "The Maxwell-Brancheau Arthroereisis (MBA) Implant in Pediatric and Adult Flexible Flatfoot Conditions", Foot and Ankle Quarterly, Winter 1999, vol. 12, No. 4.

* cited by examiner

*Primary Examiner* — Thomas J Sweet
*Assistant Examiner* — Chirstopher D Prone
(74) *Attorney, Agent, or Firm* — Faegre & Benson LLP

(57) ABSTRACT

A subtalar implant device includes a rounded end cap region, a threaded region having threads, and a core having a first end, a second end, a core exterior and a longitudinal axis. The threads can have a shape that varies between the first end and the second end of the core. For example, the threads can include an outer edge having an edge width that varies. Further, the threads can include a thread depth that can vary between the first end and the second end of the core. A thread radius of curvature varies at a different rate than a core radius of curvature. The core can define one or more core apertures that extend through the core at various angles relative to the longitudinal axis. In one embodiment, two core apertures are positioned at an angle greater than zero degrees relative to each other.

23 Claims, 2 Drawing Sheets

SUBTALAR IMPLANT ASSEMBLY

RELATED APPLICATION

This Application claims priority on U.S. Provisional Application Ser. No. 60/543,728 filed on Feb. 10, 2004 and entitled "SUBTALAR IMPLANT ASSEMBLY". The contents of U.S. Provisional Application Ser. No. 60/543,728 are incorporated herein by reference.

FIELD OF THE INVENTION

The present invention relates generally to an implant device that is used in the treatment of flatfoot deformity.

BACKGROUND

Flatfoot deformity (also referred to herein as "flatfoot") can affect persons of all ages. In children, flatfoot is the result of the inside arch of the foot becoming flattened, causing the calcaneus (heel bone) to be turned outward, thereby resulting in excessive pronation of the foot. Many cases of flatfoot deformity in children are also associated with excessive flexibility in the joints of the foot which is commonly caused by ligamentous laxity. In adults, terms such as posterior tibial tendon dysfunction or adult acquired flatfoot are used to describe a gradual but progressive and sometimes painful condition resulting in the loss of one's arch. The posterior tibial muscle stabilizes the arch and creates a rigid platform for walking and running. If the posterior tibial tendon becomes damaged or tears, the arch loses its stability and can collapse, causing flatfoot.

Various attempts to correct flatfoot deformity have not been altogether satisfactory. For example, foot orthotics, training shoes and stretching can be used and implemented. However, in relatively severe cases, these somewhat conservative treatments may not fully resolve the flatfoot condition. Further, surgical intervention including the positioning of subtalar implants between the calcaneus and the talus of the foot has also been explored. Unfortunately, various problems can arise resulting from these types of surgeries, including misplacement of the implant, unwanted movement of the implant following surgery.

SUMMARY

The present invention is directed toward a subtalar implant assembly including an implant device and an implant guide. The implant device includes a core having a first end, a second end, a core exterior that extends between the first end and the second end, and a longitudinal axis. The implant device can also include a rounded end cap region that extends away from at least one of the ends of the core. In one embodiment, the implant device includes a threaded region having threads that extend away from the core exterior. The threads can have a shape that varies between the first end and the second end of the core. For example, the threads can include an outer edge having an edge width that varies. Further, the threads can include a thread depth that is substantially perpendicular to the longitudinal axis of the core. In this embodiment, the thread depth can vary between the first end and the second end of the core.

The threads can have a thread radius of curvature that varies between the first end and the second end of the core, and the core exterior can have a core radius of curvature that varies between the first end and the second end. In one embodiment, the thread radius of curvature varies at a different rate than the core radius of curvature between the first end and the second end of the core.

In, another embodiment, the core exterior has a core angle relative to the longitudinal axis that is greater than zero degrees. The outer edge of the threads can have a plurality of edge points that are coplanar with the longitudinal axis, with these edge points forming a multiple edge angle relative to the longitudinal axis that is greater than zero degrees. In one embodiment, the multiple edge angle is greater than the core angle over at least a portion or a majority of the core between the first end and the second end.

Further, the core can define one or more core apertures that can extend through the core at various angles relative to the longitudinal axis. In one embodiment, two such core apertures are positioned at an angle greater than zero degrees relative to each other.

The present invention is also directed to a method for manufacturing a subtalar implant device.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
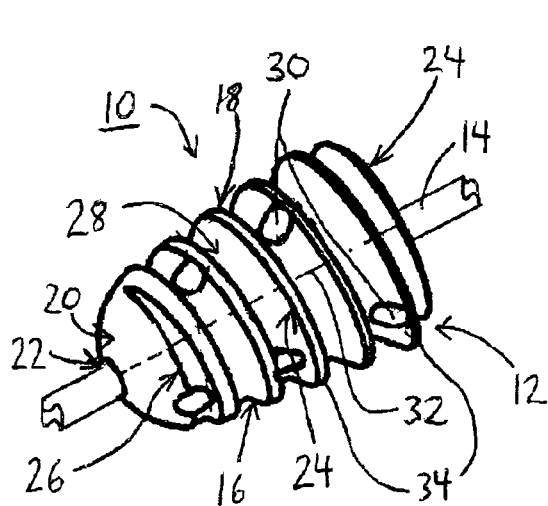
FIG. 1 is a perspective view of an embodiment of an implant assembly having features of the present invention.

FIG. 1 is a perspective view of an embodiment of an implant assembly 10 having features of the present invention. In at least one embodiment, at least a portion of the implant assembly 10 is positioned within the foot 36 (illustrated in FIG. 2) of an individual to assist in the correction of flatfoot deformity.

In the embodiment illustrated in FIG. 1, the implant assembly 10 includes an implant device 12 and an implant guide 14. In one embodiment, the implant device 12 is integrally formed as a unitary structure that includes a core region 16, a threaded region 18, an end cap region 20, and a longitudinal aperture 22. Although the implant device 12 is particularly suited to being formed as an integral structure, for convenience of discussion, the various regions are discussed separately.

The shape and size of the core region 16 can vary depending upon the design requirements of the implant assembly 10 and the foot 36 into which the implant device 12 is being positioned. In at least one embodiment, the core region 16 can include a first end 24, a second end 26, a core exterior 28, and a plurality of core apertures 30. Further, the core region 16 has a longitudinal axis 32.

The core region 16 generally has a cross-sectional area that varies along the length of the core region 16 between the first end 24 and the second end 26. More specifically, the cross-sectional area of the core region 16 taken on a plane that is substantially perpendicular to the longitudinal axis 32 can vary between the first end 24 and the second end 26. In the embodiment illustrated in FIG. 1, the core region 16 has a generally tapered shape moving from the first end 24 toward the second end 26. For example, in one embodiment, the cross-sectional area of the core region 16 can decrease moving from the first end 24 toward the second end 26, as described in greater detail below. In another embodiment, the cross-sectional area of the core region 16 can increase moving from the first end 24 toward the second end 26. In still alternative embodiments, the core region 16 can have other geometries that vary between the first end 24 and the second end 26.

The cross-sectional shape of the core region 16 can also vary. For instance, in the embodiment illustrated in FIG. 1, the core region 16 has a cross-sectional shape that is substantially circular. In alternative embodiments, the cross-sectional shape of the core region 16 can be somewhat oval, hexagonal, octagonal, triangular or can have another suitable geometry.

The material used to form the core region 16 can vary. In non-exclusive examples, the core region 16 can be formed from various plastics, metals, metal alloys, glass, ceramics, composite materials such as carbon fiber, bio-absorbable materials, or other suitable materials. In one embodiment, the core region 16 can be formed from one or more different materials. For instance, the core region 16 can be formed from a combination of metals and/or plastics.

The orientation and shape of the ends 24, 26 can vary. In one embodiment, the first end 24 can be substantially perpendicular to the longitudinal axis 32 of the core region 16, and can have a relatively flat shape. As defined herein, the second end 26 can also be substantially perpendicular to the longitudinal axis 32 of the core region 16, and can have a relatively flat shape.

The core exterior 28 is the exterior surface of the core region 16, from which the threaded region 18 extends. The threaded region 18 extends between the first end 24 and the second end 26 of the core region 16. In the embodiment illustrated in FIG. 1, the threaded region 18 extends approximately 100% of the length of the core region 16 from the first end 24 to the second end 26, excluding the end cap region 20. Alternatively, the threaded region 18 can extend less than the entire length of the core region 16. For example, in alternative embodiments, the threaded region 18 can extend at least approximately 10%, 25%, 40%, 50%, 60%, 75% or 90% of the distance between the first end 24 and the second end 26 of the core region 16.

The core apertures 30 provide channels, pathways or tunnels that allow bone, connective tissue, fibrous tissue, and/or muscle tissue to grow within the core apertures 30 to anchor the implant device 12 within the foot 36. The positioning, size and shape of the core apertures 30 can vary depending upon the design requirements of the implant device 12. In one embodiment, the one or more core apertures 30 extend at least partially through the core region 16 in a direction that is different than the longitudinal axis 32 of the core region 16. Stated another way, at least a portion of the core apertures 30 are angled relative to the longitudinal axis 32 of the core region 16. In one embodiment, the core apertures 30 are substantially perpendicular to the longitudinal axis 32 of the core region 16, and extend completely through the core region 16. In alternative embodiments, the core apertures 30 extend through the core region 16 at angles of approximately 15 degrees, 20 degrees, 30 degrees, 45 degrees, 60 degrees and 75 degrees relative to the longitudinal axis 32.

The core apertures 30 can be oriented so that at least two of the core apertures 30 are positioned to extend through the core region 16 substantially perpendicular to each other. In other words, two or more of the core apertures 30 can be offset from each other by approximately 90 degrees. In another embodiment, two or more of the core apertures 30 can be offset from each other at an angle that is greater than zero degrees. In still alternative embodiments, two or more of the core apertures 30 can be offset from each other by at least approximately 15 degrees, 30 degrees, 45 degrees, 60 degrees, 120 degrees, 150 degrees or 165 degrees. Still alternatively, the offset between any two of the core apertures 30 can be greater or less than these offsets.

The core apertures 30 can all be similar is size and shape, or they can vary within a particular implant device 12. For example, in one embodiment, the core apertures 30 can have a substantially circular shape. Moreover, in one embodiment, one or more of the core apertures 30 can have a diameter of approximately 0.080 inches. In alternative embodiments, one or more of the core apertures 30 can have a diameter that is greater or less than 0.080 inches. In alternative embodiments, the core apertures 30 can be substantially oval, triangular, rectangular, hexagonal, octagonal or can have other suitable geometries.

The threaded region 18 includes one or more threads 34 that spiral around the core exterior 28. In the embodiment illustrated in FIG. 1, the threads 34 consist of a continuous helical rib that is corkscrew-shaped and spirals around the core exterior 28. As described in greater detail below, in one embodiment, the shape of the threads 34 can vary along the length of the threads 34. With this design, the implant device 12 can be more effectively rotated into position in the foot 36. The threads 34 can also assist in securing the implant device 12 in place in the foot 36.

The material used to form the threaded region 18 can be substantially the same as the material used to form the core region 16. In one embodiment, the threaded region 18 can be formed from a material similar to that utilized in forming the core region 16. Alternatively, the material used to form the threaded region 18 can vary. For example, the threaded region 18 can be formed from various plastics, metals, metal alloys, glass, ceramics, composite materials such as carbon fiber, or other suitable materials. The threaded region 18 can be integrally molded, cast, formed by a material removal process, or otherwise shaped and/or formed with one or more of the other regions 16, 20. Alternatively, the threaded region 18 can be added to the core region 16.

The end cap region 20 can extend away from one of the ends 24, 26 of the core region 16. In the embodiment illustrated in FIG. 1, the end cap region 20 extends away from the second end 26 of the core region 16. The shape of the end cap region 20 can vary. For example, the end cap region 20 can have a somewhat rounded shape, as illustrated in FIG. 1. With this rounded end cap region 20 design, the implant device 12 can be more easily inserted within the foot 36 during a surgical procedure. In alternative embodiments, the end cap region 20 can be somewhat flat, pyramidal, or can have another suitable geometry that facilitates insertion of the implant device 12 within the foot 36.

The material used to form the end cap region 20 can be substantially the same as the material used to form one or more of the other regions 16, 18. Alternatively, the material used to form the end cap region 20 can vary. For example, the end cap region 20 can be formed from various plastics, metals, metal alloys, glass, ceramics, composite materials such as carbon fiber, or other suitable materials. The end cap region 20 can be molded, cast, or otherwise shaped and/or formed along with one or more of the other regions 16, 18. For instance, in one embodiment, the end cap region 20 can be integrally formed as a unitary structure with the core region 16. Alternatively, the end cap region 20 can be added to the core region 16.

The longitudinal aperture 22 can cooperate with the implant guide 14 to allow accurate positioning of the implant device 12 within the foot 36. In this embodiment, the longitudinal aperture 22 is sized and shaped to receive the implant guide 14, and move along the implant guide 14 during insertion of the implant device 12 into the foot 36 during a surgical procedure, as provided in greater detail below. The longitudinal aperture 22 can be somewhat cylindrical in shape as illustrated in FIG. 1, or can be another suitable shape that can fit over the implant guide 14. The longitudinal aperture 22 can be internally threaded, grooved or ridged, or the longitudinal aperture 22 can be threadless.

The longitudinal aperture 22 can extend partially or completely through the core region 16 and/or the end cap region 20 of the implant device 12. In the embodiment illustrated in FIG. 1, the longitudinal aperture 22 can be positioned substantially along the longitudinal axis 32. The longitudinal aperture 22 can provide a channel, pathways or tunnel that allows bone, connective tissue and/or muscle tissue to grow into the longitudinal aperture 22 to anchor the implant device 12 within the foot 36.

The implant guide 14 can be positioned within the foot 36 prior to insertion of the implant device 12. Once the implant guide 14 is accurately positioned, the implant device 12 can be threaded or otherwise positioned on the implant guide 14 for insertion into the foot 36. In one embodiment, the implant guide 14 can be externally threaded to accommodate the longitudinal aperture 22 of the implant device 12. Alternatively, the implant guide 14 can include grooves or ridges that can align with grooves or ridges of the longitudinal aperture 22. Still alternatively, the implant guide 14 can have a relatively smooth surface. Following insertion of the implant device 12 into the foot 36, the implant guide 14 can be removed.

Figure 2:
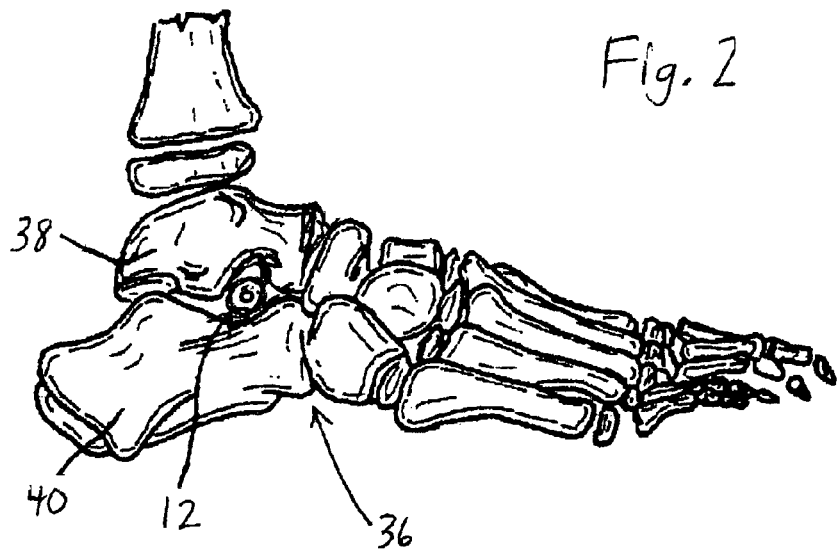
FIG. 2 is a lateral view of the bones of a foot and a portion of the implant assembly illustrated in FIG. 1.

FIG. 2 is a lateral view of the implant device 12 having features of the present invention, illustrated in an implanted position within a simplified representation of the bones of a typical foot 36. More specifically, the implant device 12 illustrated in FIG. 1 is positioned substantially between a talus 38 and a calcaneus 40 of the foot 36.

Figure 3:
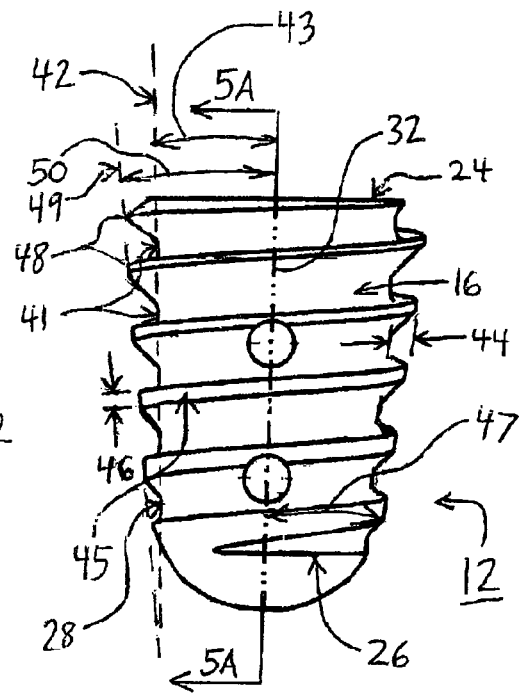
FIG. 3 is a side view of the implant device illustrated in FIG. 1.

FIG. 3 is a side view of the implant device 12 illustrated in FIG. 1. In this embodiment, the core exterior 28 is angled relative to the longitudinal axis 32. The angle formed between the longitudinal axis 32 and any two or more core points 41 (two representative core points 41 are illustrated in FIG. 3) along the core exterior 28 that are taken along a line 42 (one representative dashed line 42 is illustrated in FIG. 3) that is coplanar with the longitudinal axis 32 is referred to herein as a core angle 43. In one embodiment, the core exterior 28 can have a relatively constant core angle 43 between the first end 24 and the second end 26 of the core region 16.

Alternatively, the core exterior 28 can have one or more core angles 42 that vary between the first end 24 and the second end 26 of the core region 16. In the embodiment illustrated in FIG. 3, the core angle 43 is greater than zero degrees. Stated another way, the core exterior 28 has a core radius of curvature that varies between the first end 24 and the second end 26 of the core region 16. In the embodiment illustrated in FIG. 3, the core radius of curvature decreases from the first end 24 toward the second end 26. In alternative embodiments, the core radius of curvature can increase from the first end 24 toward the second end 26, or the core radius of curvature can be substantially constant between the first end 24 and the second end 26.

Stated yet another way, the core exterior 28 can have a plurality of substantially circular cross-sections with radii that vary over the length of the core region 16 between the first end 24 and the second end 26. In the embodiment illustrated in FIG. 3, the radii of these cross-sections decrease from the first end 24 toward the second end 26 of the core region 16. However, the radii of these cross-sections can increase from the first end 24 toward the second end 26, or the radii of these cross-sections can be substantially constant between the first end 24 and the second end 26 of the core region 16.

In another embodiment, the core angle 43 is greater than approximately zero degrees and less than approximately 30 degrees. In another embodiment, the core angle 43 is greater than approximately one degree and less than approximately 15 degrees. In another embodiment, the core angle 43 is greater than approximately two degrees and less than approximately five degrees. In another embodiment, the core angle 43 is approximately three degrees. With these designs, the somewhat tapered shape of the core exterior 28 allows the implant device 12 to be more easily inserted into the foot 36 between the talus 38 and the calcaneus 40. It is recognized that these examples are only representative of various possible core angles 43, and are not intended to be exclusive examples.

In the embodiment illustrated in FIG. 3, the threads 34 have a thread depth 44 and an outer edge 45 having an edge width 46. As used herein, the thread depth 44 is the distance between the outer edge 45 of the threads 34 and the core exterior 28, measured at an angle that is substantially perpendicular to the longitudinal axis 32. The thread depth 44 is measured at any specific location along the length of the threads 34, and is specific to that location as set forth in greater detail below.

In one embodiment, the outer edge 45 is angled relative to the longitudinal axis 32. The outer edge 45 and the longitudinal axis 32 form a local edge angle 47 at any particular location along the length of the threads 34 that can vary from one portion of the threads 34 to another. In alternative embodiments, the local edge angle 47 at each location along the length of the threads 34 can be substantially similar or identical.

Moreover, as illustrated in FIG. 3, the outer edge 45 can include two or more edge points 48 along the outer edge 45 that are taken along a line 49 (one such representative dashed line 49 is illustrated in FIG. 3) that is coplanar with the longitudinal axis 32 can be positioned at a multiple edge angle 50 relative to the longitudinal axis 32 of the core region 16. The multiple edge angle 50 can be relatively constant or it can vary between the first end 24 and the second end 26 of the core region 16. In one embodiment, the multiple edge angle 50 is different than the core angle 43 over at least a corresponding portion of the length of the core region 16. In alternative embodiments, the multiple edge angle 50 is different than the core angle 43 over a majority of the length of the core region 16, or over the entire length of the core region 16.

For example, in alternative embodiments, the multiple edge angle 50 can be at least approximately 10%, 25%, 50%, 75%, 100%, 133%, 150%, 200%, 250%, 300%, 400% or 500% greater than the core angle 43 over at least a corresponding portion of the length of the core region 16, over a majority of the length of the core region 16, or over the entire length of the core region 16. Alternatively, the multiple edge angle 50 can be a different percentage greater than the core angle 43 over a corresponding portion of the length of the core region 16, over a majority of the length of the core region 16, or over the entire length of the core region 16. Still alternatively, the multiple edge angle 50 can be less than the core angle 43 over at least a corresponding portion of the length of the core region 16, over a majority of the length of the core region 16, or over the entire length of the core region 16.

In the embodiment illustrated in FIG. 3, the multiple edge angle 50 is greater than zero degrees. Stated another way, the threads 34 can have a thread radius of curvature that varies between the first end 24 and the second end 26 of the core region 16. Further, the thread radius of curvature can vary at a different rate than the core radius of curvature over at least a portion of the core region 16. In one embodiment, the thread radius of curvature can vary at a different rate than the core radius of curvature over the entire core region 16 between the first end 24 and the second end 26.

In another embodiment, the multiple edge angle 50 is greater than approximately zero degrees and less than approximately 45 degrees. In another embodiment, the multiple edge angle 50 is greater than approximately two degrees and less than approximately 30 degrees. In another embodiment, the multiple edge angle 50 is greater than approximately four degrees and less than approximately ten degrees. In another embodiment, the multiple edge angle 50 is approximately seven degrees. As set forth in greater detail below, this design results in the threads 34 having an increasing thread depth moving from the second end 26 toward the first end 24 of the core region 16. It is recognized that these examples are only intended to be representative of the multiple edge angle 50, and are not meant to be exclusive examples.

Figure 4:
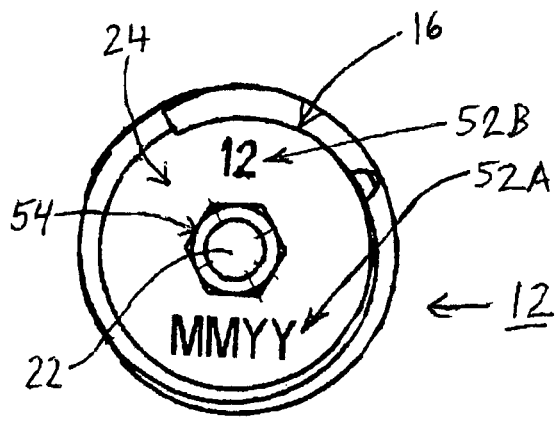
FIG. 4 is an end view of the implant device illustrated in FIG. 1.

FIG. 4 is an end view of an embodiment of the implant device 12 which illustrates the first end 24 of the core region 16. In this embodiment, the first end 24 can include identifying markings 52A, 52B such as the approximate date of manufacture or the date of installation of the implant device 12, and/or the lot number of the implant device 12, as non-exclusive examples. Additionally, the longitudinal aperture 22 can include an expanded region 54, which can have a somewhat hexagonal shape at or near the first end 24 of the core region 16 to receive a tool (not shown) that can be used to move the implant device 12 along the implant guide 14 (illustrated in FIG. 1).

Figure 5A:
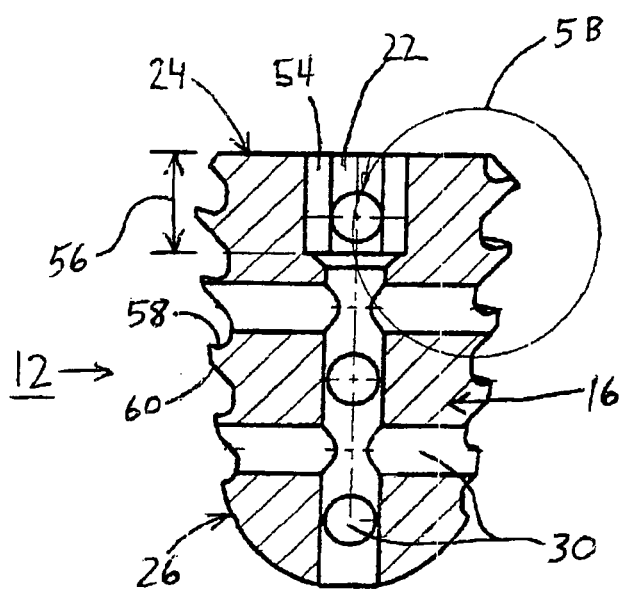
FIG. 5A is a cross-sectional view of the implant device taken on line 5A-5A in FIG. 3.

FIG. 5A is a cross-sectional view of the implant device 12 taken on line 5A-5A in FIG. 3. In this embodiment, the implant device 12 includes five core apertures 30 that extend through the core region 16. It is recognized that any suitable number of core apertures 30 can be used with the implant device 12 provided herein.

Further, the expanded region 54 of the longitudinal aperture 22 can extend from the first end 24 toward the second end 26 a distance 56 that can vary depending upon the design requirements of the implant device 12.

Additionally, FIG. 5A illustrates that in one embodiment, the threads are not necessarily V-shaped, but have a cupped region 58 and a tapered region 60. With this design, the implant device 12 is less susceptible to expulsion or backing out from between the talus 38 and the calcaneus 40 once the implant device 12 is positioned within the foot 36.

Figure 5B:
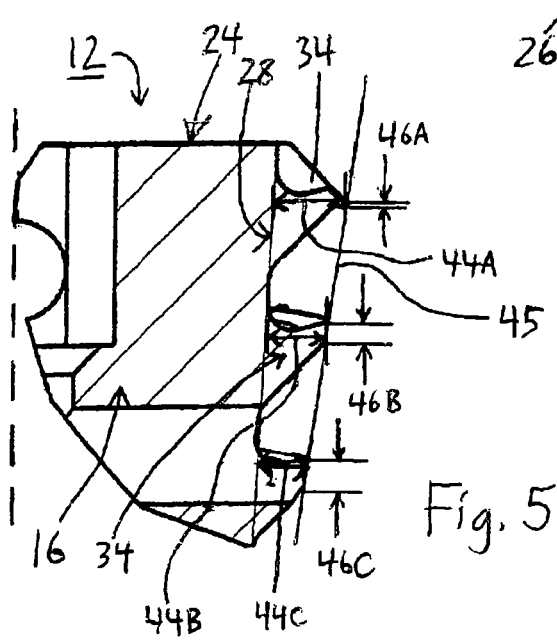
FIG. 5B is a detailed view of a portion of the implant device illustrated in circle 5B in FIG. 5A.

FIG. 5B is a detailed view of the portion of the implant device 12 taken within circle 5B in FIG. 5A. In this embodiment, FIG. 5B more closely illustrates the difference between the angle of the core exterior 28 and the angle of the outer edge 45 of the threads 34.

In addition, in this embodiment, the thread depth 44 can vary between the first end 24 and the second end 26 of the core region 16. For example, FIG. 5B shows three separate portions of adjacent threads 34 which have three corresponding thread depths 44A, 44B, 44C that differ. In this embodiment, the thread depths 44A, 44B, 44C decrease moving from the first end 24 toward the second end 26 (illustrated in FIG. 5A) of the core region 16. In an alternative embodiment, the thread depths 44A, 44B, 44C can also, or alternatively, increase moving from the first end 24 toward the second end 26 of the core region 16. In alternative embodiments, the thread depth 44 can vary between two or more adjacent threads 34 by at least approximately 1%, 2%, 5%, 10%, 20%, 50%, 75% or 100%.

Moreover, FIG. 5B illustrates that in this embodiment, the edge width 46 can vary along the length of the threads 34. For example, FIG. 5B shows three separate portions of adjacent threads 34 which have three corresponding edge widths 46A, 46B, 46C that differ. In this embodiment, the edge widths 46A, 46B, 46C increase moving from the first end 24 toward the second end 26 of the core region 16. In alternative embodiments, the edge widths 46A, 46B, 46C can also, or alternatively, decrease moving from the first end 24 toward the second end 26 of the core region 16. In alternative embodiments, the edge width 46 can vary between adjacent threads 34 by at least approximately 1%, 2%, 5%, 10%, 20%, 50%, 75% or 100%.

While the particular implant assembly 10 as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A subtalar implant device adapted for implantation between a talus and a calcaneus of a foot, the subtalar implant comprising:
   a core region having a first end configured for insertion into the foot, a second end, a core exterior that extends between the first end and the second end, and a longitudinal axis, the core exterior sized and shaped to be positioned substantially between the talus and the calcaneus, and the core exterior having a core angle relative to the longitudinal axis;
   a threaded region formed on and extending away from the core exterior, the threaded region including threads having an outer edge with a plurality of edge points located in a single plane that is coplanar with the longitudinal axis, the edge points comprise a multiple edge angle relative to the longitudinal axis, wherein the core angle is less than the multiple edge angle and greater than zero degrees over at least a portion of the core region between the first end and the second end, wherein the core region and the threaded region are integrally formed as a unitary structure, wherein the outer edge includes an edge width, and wherein the edge width increases along at least a portion of the threads from the second end toward the first end; and
   an implant guide adapted for insertion completely through a longitudinal aperture in the core region to guide the subtalar implant between the talus and the calcaneus.

2. The subtalar implant device of claim 1, wherein a distance between the longitudinal axis and each of the plurality of edge points increases from the first end toward the second end.

3. The subtalar implant device of claim 1, wherein the threaded region includes a thread depth that is measured substantially perpendicularly to the longitudinal axis of the core region, the thread depth increasing from the first end toward the second end of the core region.

4. The subtalar implant device of claim 1 wherein the threaded region comprises a cupped region and a tapered region.

5. The subtalar implant device of claim 1 wherein the multiple edge angle is greater than the core angle over at least a majority of the core region between the first end and the second end.

6. The subtalar implant device of claim 1 further comprising a rounded end cap region that extends away from the first or second end.

7. The subtalar implant device of claim 1 wherein the core region defines a core aperture that extends through the core region at an angle relative to the longitudinal axis.

8. The subtalar implant device of claim 1 wherein the core region defines two core apertures that each extends through the core region at a corresponding angle relative to the longitudinal axis, and wherein the two core apertures are positioned at an angle greater than zero degrees relative to each other.

9. The subtalar implant device of claim 1 wherein the core region comprises a first material and the threaded region comprises a second material.

10. The subtalar implant device of claim 1 comprising at least two different size subtalar implant devices.

11. The subtalar implant device of claim 1 wherein the implant guide and the longitudinal aperture are threaded, and wherein the implant guide is engaged with threads in the longitudinal aperture in the core region.

12. A subtalar implant device adapted for implantation between a talus and a calcaneus of a foot, the subtalar implant comprising:
a core region having a first end, a second end adapted for insertion into the foot, a core exterior with a core radius of curvature that varies between the first end and the second end, and a longitudinal axis, the core exterior sized and shaped to be positioned substantially between the talus and the calcaneus;
a threaded region that is formed on and extends away from the core exterior, the threaded region including threads having a thread radius of curvature that varies between the first end and the second end at a different rate than the core radius of curvature, wherein the threads include a thread depth that is measured substantially perpendicularly to the longitudinal axis of the core region, the thread depth decreasing from the first end toward the second end of the core region, wherein the threads include an outer edge having an edge width that increases along the core region from the first end toward the second end, wherein the threads comprise a cupped region and a tapered region and wherein the core region and the threaded region are integrally formed as a unitary structure; and
an implant guide adapted for insertion completely through a longitudinal aperture in the core region to guide the subtalar implant between the talus and the calcaneus.

13. The subtalar implant device of claim 12 comprising an expanded region on the first end adapted to receive a tool to move the subtalar implant device along the implant guide.

14. The subtalar implant device of claim 12 wherein the outer edge further includes a plurality of edge points located in a single plane that is coplanar with the longitudinal axis, the edge points forming a multiple edge angle relative to the longitudinal axis that is greater than zero degrees.

15. The subtalar implant device of claim 14 wherein the core exterior has a core angle relative to the longitudinal axis that is greater than zero, and wherein the multiple edge angle is greater than the core angle over at least a majority of the length of the core region.

16. The subtalar implant device of claim 12 further comprising a rounded end cap region that extends away from one of the ends of the core region.

17. The subtalar implant device of claim 12 wherein the core region defines two core apertures that each extends through the core region at a corresponding angle relative to the longitudinal axis, the two core apertures being positioned at an angle greater than zero degrees relative to each other.

18. A subtalar implant device adapted for implantation between a talus and a calcaneus of a foot, the subtalar implant comprising:
a core region including a first end, a second end, a core exterior and a longitudinal axis, the core exterior having a plurality of substantially circular cross-sections each having a radius, a plurality of the radii of the cross-sections varying between the first end and the second end, the core exterior sized and shaped to be positioned substantially between the talus and the calcaneus;
threads including an outer edge having an edge width;
a rounded end cap region that extends away from the second end and is adapted for insertion into the foot, wherein the core region and the rounded end cap region are integrally formed as a unitary structure, and wherein the edge width increases along the threads from the first end toward the second end; and
an implant guide adapted for insertion completely through a longitudinal aperture in the core region to guide the subtalar implant between the talus and the calcaneus.

19. The subtalar implant device of claim 18 wherein the radius of the circular cross-section near the first end is greater than the radius of the circular cross-section near the second end.

20. The subtalar implant device of claim 18, wherein the threads are comprised by a threaded region that extends away from the core exterior, the threads having a thread radius of curvature that varies between the first end and the second end of the core region, and wherein the core exterior has a core radius of curvature that varies between the first end and the second end, the thread radius of curvature varying at a different rate than the core radius of curvature.

21. The subtalar implant device of claim 20 wherein the threads include a thread depth that is measured substantially perpendicularly to the longitudinal axis of the core region, the thread depth decreasing from the first end toward the second end of the core region.

22. The subtalar implant device of claim 20 wherein the threads include an outer edge having a plurality of edge points that are located in a single plane that is coplanar with the longitudinal axis, the edge points forming a multiple edge angle relative to the longitudinal axis that is greater than zero degrees, the core exterior having a core angle relative to the longitudinal axis that is greater than zero degrees, and wherein the multiple edge angle is greater than the core angle over at least a majority of the length of the core region.

23. A subtalar implant device adapted for implantation between a talus and a calcaneus of a foot, the subtalar implant comprising:
a core region comprising a first end, a second end configured for insertion into the foot, a core exterior that tapers inward from the first end to the second end, and a longitudinal axis, the core exterior sized and shaped to be positioned substantially between the talus and the calcaneus; and
a threaded region formed on and extending away from the core exterior, the threaded region including threads having a plurality of edge points located in a single plane that is coplanar with the longitudinal axis, the edge points comprise a multiple edge angle relative to the longitudinal axis that is greater than zero degrees over at least a portion of the core region between the first end and the second end, wherein the threaded region includes an outer edge having an edge width that increases along the core region from the first end toward the second end.

* * * * *